US007960570B2

(12) United States Patent
Hamilton et al.

(10) Patent No.: US 7,960,570 B2
(45) Date of Patent: Jun. 14, 2011

(54) SMALL MOLECULE INHIBITORS OF ROTAMASE ENZYME ACTIVITY

(75) Inventors: Gregory S. Hamilton, Catonsville, MD (US); Joseph Steiner, Hampstead, MD (US)

(73) Assignee: GliaMed, Inc., Dobbs Ferry, NY (US)

( * ) Notice: Subject to any disclaimer, the term of this patent is extended or adjusted under 35 U.S.C. 154(b) by 0 days.

(21) Appl. No.: 12/633,464

(22) Filed: Dec. 8, 2009

(65) Prior Publication Data

US 2010/0145071 A1    Jun. 10, 2010

Related U.S. Application Data

(60) Continuation of application No. 11/871,358, filed on Oct. 12, 2007, now Pat. No. 7,652,060, which is a continuation of application No. 11/166,220, filed on Jun. 27, 2005, now Pat. No. 7,282,510, which is a division of application No. 10/219,887, filed on Aug. 16, 2002, now abandoned, which is a continuation of application No. 09/605,475, filed on Jun. 28, 2000, now Pat. No. 6,500,959, which is a continuation of application No. 08/833,629, filed on Apr. 8, 1997, now Pat. No. 6,140,357, which is a continuation of application No. 08/650,461, filed on May 21, 1996, now Pat. No. 5,859,031, which is a continuation-in-part of application No. 08/479,436, filed on Jun. 7, 1995, now Pat. No. 5,614,547.

(51) Int. Cl.
C07D 207/16    (2006.01)
(52) U.S. Cl. .................................................. 548/533
(58) Field of Classification Search .................. None
See application file for complete search history.

(56) References Cited

U.S. PATENT DOCUMENTS

| | | | |
|---|---|---|---|
| 3,795,738 A | 3/1974 | Plotnikoff |
| 3,810,884 A | 5/1974 | Gold |
| 3,917,840 A | 11/1975 | Gold |
| 4,070,361 A | 1/1978 | Petrillo, Jr. |
| 4,128,653 A | 12/1978 | Cushman et al. |
| 4,310,461 A | 1/1982 | Krapcho et al. |
| 4,321,269 A | 3/1982 | Wareing |
| 4,374,829 A | 2/1983 | Harris et al. |
| 4,390,695 A | 6/1983 | Krapcho et al. |
| 4,431,644 A | 2/1984 | Smith et al. |
| 4,472,380 A | 9/1984 | Harris et al. |
| 4,501,901 A | 2/1985 | Thottathil et al. |
| 4,507,292 A | 3/1985 | Heywang et al. |
| 4,531,964 A | 7/1985 | Shimano et al. |
| 4,574,079 A | 3/1986 | Gavras et al. |
| 4,578,474 A | 3/1986 | Krapcho et al. |
| 4,593,102 A | 6/1986 | Shanklin, Jr. |
| 4,604,402 A | 8/1986 | Godfry, Jr. et al. |
| 4,649,147 A | 3/1987 | Mueller et al. |
| 4,708,954 A | 11/1987 | Ienaga et al. |
| 4,762,821 A | 8/1988 | Nestor |
| 4,766,110 A | 8/1988 | Ryan et al. |
| 4,808,573 A | 2/1989 | Gold et al. |
| 4,818,749 A | 4/1989 | Gold et al. |
| 4,912,231 A | 3/1990 | Kronenthal et al. |
| 5,002,963 A | 3/1991 | De Luca et al. |
| 5,147,877 A | 9/1992 | Goulet |
| 5,192,773 A | 3/1993 | Armistead et al. |
| 5,204,338 A | 4/1993 | Baader et al. |
| 5,252,579 A | 10/1993 | Skotnicki et al. |
| 5,294,603 A | 3/1994 | Rinehart |
| 5,319,098 A | 6/1994 | Burbaum et al. |
| 5,330,993 A | 7/1994 | Armistead et al. |
| 5,348,944 A | 9/1994 | Gold et al. |
| 5,359,138 A | 10/1994 | Takeuchi et al. |
| 5,385,918 A | 1/1995 | Connell et al. |
| 5,414,083 A | 5/1995 | Hacki et al. |
| 5,424,454 A | 6/1995 | Burbaum et al. |
| 5,447,915 A | 9/1995 | Schreiber et al. |
| 5,516,797 A | 5/1996 | Armistead et al. |
| 5,543,423 A | 8/1996 | Zelle et al. |
| 5,589,499 A | 12/1996 | Weth |
| 5,614,547 A | 3/1997 | Hamilton et al. |
| 5,620,971 A | 4/1997 | Armistead et al. |
| 5,622,970 A | 4/1997 | Armistead et al. |
| 5,661,167 A | 8/1997 | Peet et al. |
| 5,696,135 A | 12/1997 | Steiner et al. |
| 5,721,256 A | 2/1998 | Hamilton et al. |
| 5,726,184 A | 3/1998 | Zelle |
| 5,780,484 A | 7/1998 | Zelle et al. |
| 5,786,378 A | 7/1998 | Hamilton et al. |
| 5,795,908 A | 8/1998 | Hamilton et al. |
| 5,798,355 A | 8/1998 | Steiner et al. |

(Continued)

FOREIGN PATENT DOCUMENTS

DE    3508251    9/1986

(Continued)

OTHER PUBLICATIONS

Ando, Takao et al., "Formation of Crossed Phenzine from the Reactions between Tetra-p-anisyl- and Tetra-p-tolyl-hydrazines in Liquid Sulphur Dioxide," Chem. Comm., S. Chem. Comm., 1975, 989.

Andrus, Merrit B., Structure-based design of an acyclic ligand that bridges FKBP12 and calcineurin, J. Am. Chem. Soc., 1993, 115(2), 10420-1.

Armistead, D.M. et al., "Design, synthesis and structure of non-macrocyclic inhibitors of FKBP12, the major binding protin for the immunosuppressant FK506," Acta Crystallogr. 1995, D5I(4), 522-8.

Askin, D. et al., "Chemistry of FK-506: benzilic acid rearrangement of the tricarbonyl system," Tetrahedron Lett., 1989,30(6), 671-4.

Askin, D. et al., "Effecient Degradation of FK-506 to a versatile synthetic intermediate," J. Org. Chem., 1990, 55(20), 5451-4.

(Continued)

*Primary Examiner* — Kamal A Saeed
(74) *Attorney, Agent, or Firm* — Dennis A. Bennett; Cynthia Hathaway

(57) ABSTRACT

This invention relates to neurotrophic compounds having an affinity for FKBP-type immunophilins, their preparation and use as inhibitors of the enzyme activity associated with immunophilin proteins, and particularly inhibitors of peptidyl-prolyl isomerase or rotamase enzyme activity.

17 Claims, No Drawings

U.S. PATENT DOCUMENTS

| | | | |
|---|---|---|---|
| 5,801,187 | A | 9/1998 | Li et al. |
| 5,801,197 | A | 9/1998 | Steiner et al. |
| 5,811,434 | A | 9/1998 | Zelle et al. |
| 5,840,736 | A | 11/1998 | Zelle et al. |
| 6,037,370 | A | 3/2000 | Armistead |
| 6,124,328 | A | 9/2000 | Armistead |
| 7,153,883 | B2 | 12/2006 | Hamilton et al. |
| 2008/0076817 | A1 | 3/2008 | Hamilton et al. |

FOREIGN PATENT DOCUMENTS

| | | |
|---|---|---|
| DE | 3931051 | 3/1990 |
| DE | 4015255 | 11/1991 |
| EP | 12401 | 6/1980 |
| EP | 48159 | 3/1982 |
| EP | 50800 | 5/1982 |
| EP | 73143 | 3/1983 |
| EP | 88350 | 9/1983 |
| EP | 196841 | 10/1986 |
| EP | 260118 | 3/1988 |
| EP | 333174 | 9/1989 |
| EP | 352000 | 1/1990 |
| EP | 378318 | 7/1990 |
| EP | 405994 | 1/1991 |
| EP | 419049 | 3/1991 |
| EP | 468339 | 1/1992 |
| EP | 564924 | 10/1993 |
| EP | 572365 | 12/1993 |
| EP | 652229 | 5/1995 |
| GB | 2247456 | 3/1992 |
| JP | 4149166 | 5/1992 |
| JP | 5178824 | 7/1993 |
| WO | 8809789 | 12/1988 |
| WO | 9012805 | 11/1990 |
| WO | 9104985 | 4/1991 |
| WO | 9113088 | 9/1991 |
| WO | 9200278 | 1/1992 |
| WO | 9203472 | 3/1992 |
| WO | 9204370 | 3/1992 |
| WO | 9216501 | 10/1992 |
| WO | 9218478 | 10/1992 |
| WO | 9219593 | 11/1992 |
| WO | 9219745 | 11/1992 |
| WO | 9221313 | 12/1992 |
| WO | 9307269 | 4/1993 |
| WO | 9313066 | 7/1993 |
| WO | 9323548 | 11/1993 |
| WO | 9325546 | 12/1993 |
| WO | 9405639 | 3/1994 |
| WO | 9407858 | 4/1994 |
| WO | 9413629 | 6/1994 |
| WO | 9512572 | 5/1995 |
| WO | 9524385 | 9/1995 |
| WO | 9526337 | 10/1995 |
| WO | 9535308 | 12/1995 |
| WO | 9535367 | 12/1995 |
| WO | 9606097 | 2/1996 |
| WO | 9615101 | 5/1996 |
| WO | 9617816 | 6/1996 |
| WO | 9633184 | 10/1996 |
| WO | 9636630 | 11/1996 |
| WO | 9641609 | 12/1996 |
| ZA | 9207782 | 4/1993 |

OTHER PUBLICATIONS

Baader, Ekkehard et al., "Inhibition of prolyl 4-hydroxylase by oxalyl amino acid derivatives in vitro, in isolated microsomes and in embryonic chicken tissues," Biochem. J., 1994, 300(2), 525-30.

Baumann, K. et al., "Synthesis and oxidative cleavage of the major equilibrium products of ascomycin and Fk 506," Tetrahedron Lett., 1995, 26(13), 2231-4.

Bender, D., et al., "Periodate oxidation of α-keto γ-lactams. Enol oxidation and β-lactam formation. Mechanism of periodate hydroxylation reactions," J. Org. Chem., 1978, 43(17), 3354-62.

Birkenshaw, Timothy N. etal. "Synthetic FKBP12 Ligands. Design and Synthesis of Pyranose Replacements," Bioorganic & Medicinal Chemistry Letters, 1994, vol. 4, No. 21, pp. 2501-2506.

Blaschke et al., Chemical abstracts, 1974. 85, 78405k.

Boulmedais, Au et al., "Stereochemistry of Electrochernical Reduction of Optically Active a-ketoamides. II. Electroreduction of benzoylformamides derived from S-(–)-proline," Bull. Soc. Chim. Fr., 1989, (2), 185-91.(French).

Bycroft, Bame W., and Lee Grahame R., "Efficient asymmetric synthesis of γ-amino from γ-keto acids and ammonia with conservation of the chiral reagent," J. Chem. Soc., 1975, 24, 988-9.

Caffrey, Moya V. et al. "Synthesis and Evaluation of Dual Domain Macrocyclic FKBP12 Ligands," Bioorganic & Medicinal Chemistry Letters, 1994, vol. 4, No. 21, pp. 2507-2510.

Cameron, Andrew et al., "Immunophilin FK506 binding protein associated with inositol 1,4,5-tnphosphate receptor modulates calcium flux," Proc. Natl. Acad. Sci. USA, 1995, 92, 1784-1 788.

Caufield, Craig E. and Musser, John H., Annual Reports in Medicinal Chemistry, Johns (Ed.). Academic Press, Inc., Chapter 21, 195-204,1989.

Chakaraborty, Tushar K., "Studies towards the development of cyclic peptide-based analogs of macrolide immunosuppressants," Pure Appl. Chem., 1996, 68(3), 565-568.

Chakraborty, TK et al., "Design and Synthesis of a rapamycin-based high affinity binding FKBP12 ligand," Chem. Biol., 1995, 2(3), 157-61.

Coleman, R., and Danishefsky, S., "Degradation and manipulations of the immunosuppressant FK506: preparation of potential synthetic Intermediates," Heterocycles, 1989, 28(1), 157-61.

Colombo, L. et al., "Enantiosetective synthesis of secondary alcohols in the pressence of chiral ligands," Tetrahedron, 1982. 38(17), 2725-7.

Cunliffe, C. Jane et al., "Novel inhibitors of prolyl 4-hydroxylase. 3. Inhibition by the substrate analog N-,oxaloglycine and its derivatives," J. Med. Chem., 1992, 35 (14). 2652-8.

Cushman, D.W. et al., Design of potent competitive inhibitors of angiotensin-converting enzyme. Carboxyalkanoyl and mercaptoalkanoyl amino acids. Biochemistry. 1977, 16(25), 5484-91.

Dawson, T.M. et al., The immunophilins, FK506 binding and cyclophilin, are discretely localized in the brain: relationship to calcineurin, Neuroscience, 1994, 62(2), 569-80.

Dawson, Ted M. et al., "Immunosuppressant FK506 enhances phosphorylation of nitric oxide synthase and protects against glutamate neurotoxicity," Proc. Natl. Acad. Sci. USA, 1993, 90, 9808-12.

Dragovich et al., "Structured-Based Design of Novel, Urea-Containing FKBP123 Inhibitors," J. Med. Chem., 1996, 39, 1872-1 884.

Dumont, F.J. "The Immunosuppressive and Toxic Effects of FK-506 are Mechanistically Related: Pharmacology of a Novel Antagonist of FK-506 and Rapamycin," J. Exp. Med., 176 (1992) 751-60.

Effenberger F. et al., Diastereoselective addition of benzenesulfenyl chloride to 1-acryloylproline esters, Chemical Abstracts, 1989, 10, 778-9.

Egbertson, M. and Danishefsky, S., "A synthetic route to the tncarbonyl region of FK-506," J. Org. Chem., 1989, 54 (1), 11-12.

Faelth, Lars et al., "Interactions between C=S groups in 1,2- and 1.3-bis(thiocarbonyl) Compounds: A Study by Spectroscopy, X-Ray Crystalllography, and CNDO/S Calculations," Theochem, 1989, 55, 239-59.

Feutren, Gilles, "The Optimal use of Cyclosporin A in Autoimmune Diseases," J. of Autoimmunity, 1992, 5, 183-95.

Finberg, Robert W. et al., "Prevention of HIV-1 Infection and Preservation of CD4 Function by the Binding of CPFs toqpI2o," Science, 1990, 249,287-91.

Fisher, Matthew at., "On the remarkable propensity for carbon-carbon bond cleavage reactions in the C(8)-C(1O) region of Fk-506," J. Org. Chem., 1991, 56(8), 2900-7.

Fry, Lionel, Psoriasis: Immunopathology and Long-term treatment with Cyclosporin, J. of Autoimmunity, 1992, 5, 277-83.

Furber, M. et al., Studies relating to the immunosuppressive activitiy of FK506, Tetrahedron Lett., 1993, 34(8), 1351-4.

Furber. Mark. "FKBP-12-ligand-calceineurin interactions: analogs of SBL506," J. Am. Chem. Soc., 1995, 117(27), 7267-8.

Gold et al, ~The Immunosuppressant FK506 increases functional recovery and nerve regeneration following peripheral nerve injury, Restorative Neurology and Neuroscience, 1994. 6, 287-296.

Gold et al., "Regulation of the transcription factor c-JUN by nerve growth factor in adult sensory neurons," Neuroscience Letters 154, 1993, 129-133.

Gold et al., The Immunosuppressant FK506 Increases the Rate of Axonai Regeneration in Rat Sciatic Nerve, The Journal of Neuroscience, 1995, 15(11), 7509-7516.

Gold, B. et at., "Regulation of aberrant neurofilarnent phosporylation in neuronal penkarya. IV. Evidence for the involvement of two signals," Brain Research, 626 (1993) 23-30.

Gold, et al, "Multiple signals underlie the anatomy-induced up-regulation of c-JUN in adult sensory neurons," Neuroscience Letters 176, 1994, 123-127.

Goulet. Mark T. and Boger, Joshua, Degradation studies on the tncarbonyl containing macrolide rapamycin, Tetrahedron Left., 1991, 32(45), 6454.

Goulet, Mark T. et al., "Construction of the FK-506 analog from rapamycin-derived materials," Tetrahedron Lett., 1991, 32(36). 4627-30.

Goulet, Mark T., and Boger, Joshua, "Degradation studies on the tncarbonyl containing macrolide rapamycin," Tetrahedron Lett., 1990, 31(34), 4845-8.

Haeusler, Johannes and Schmidt, Ulrich, "Amino acids and peptides. IX. Pyruvoyl amino acids," Chem. Ber., 1974, 107(1), 145-51. (German).

Harding, M.W., et al., "A receptor for the Immunosuppressant FK506 Is a cis-trans peptidyl-protyl isomerase," Nature Left., 1989, 341. 758-60.

Hauske, James R. et al., "Design and Synthesis of Novel FKBP Inhibitors," J. Med. Chem., 1992, 35, pp. 4284-4296.

Hauske, James R. et at., "Investigation of the effects of synthetic, non-cytotoxic immunophilin inhibitors on MDR," Bioorg. Med. Chem. Left., 1994, 4(17), 2097-102.

Hausler, Johannes, et at., Hydroxylsubstituierte Cyclodipeptide durch Ringschlafl von Pyruvoylaminosaureamiden, Chem. Ber. 107: 2804-15 (1974).

Hayward, C.M. et al., "Total Synthesis of rapamycin via a novel titanium-mediated aldol macrocyclization reaction"J. Am. Chem. Soc., 1993, 115(20), 9345-6.

Hearn, Walter R., and Worthington, Robert E., L-Proline-N-oxalic anhydnde, J. Org. Chem., 1967, 32(12), 4072-4.

Holt, Dennis A. et al. "Design, Synthesis, and Kinetic Evaluation of High-Affinity FKBP Ligands and the X-ray Crystal Structures of Their Complexes with FKBP12," J. Am. Chem. Soc., 1993, 115, pp. 9925-9938.

Holt, Dennis A. et al. Structure-Activity Studies of Synthetic FKBP Ligands as Peptidyl-Prolyl Isomerase Inhibitors, Bioorganic & Medicinal Chemistry Letters, 1994, vol. 4, No. 2, pp. 315-320.

Holt, Dennis A. et al., Structure-Activity Studies of Nonmacrocyclic Rapamycin Derivatives, Bioorganic & Medical Chemistry Letters, 1993, vol. 3, No. 10, pp. 1977-1980.

Hovarth, R., et al., "An application of the Evans-Prasad 1,3-Syn diol synthesis to a stereospecific synthesis of the C10-C27 segment of rapamycin," Tetrahedron Lett., 1993. 34(25), 3993-3996.

Iwabuchi, T. et al. "Effects of immunosuppressive peptidyl-propyl cis-trans isomerase (PPlase) inhibitors, cyclosporin A, FK506, ascomycin and rapamycin, on hair growth initiation in mouse: immunosuppression is not required for new hair growth," J. of Dermatol. Sci., (1995) 9:1, 64-69.

Jasperse, C. et al., "Sequential Radical Cyclization Approach to Propellane Triquinases. Total Synthesis of (±)-Modhephene," J. Am. Chem. Soc., 112 (1990) 5601.

Jiang, H. et al. "Induction of Anagen in Telogen Mouse Skin by Topical Application of FK505, a Potent Immunosuppressant," J. Invest. Dermatol., (1995)104:4, 523-525.

Jones, A. et al., "A formal synthesis of FK-506. Exploration of some alternatives to macrolactamization," J. Org. Chem., 1990, 55(9), 2786-97.

Jones, T. et al., "Chemistry of tncarbonyl hemiketals and application of Evans technology to the total synthesis of the immunosuppressant (-)-FK-506,"J. Am. Chem. Soc., 1990, 112(8), 2998-3017.

Kaczmar, et at., Makromol. Chem., 1976, 177, 1981-9.

Karle, Isabella L. et at., "Conformation of the oxalamide group in retro-bispeptides. Three crystal structures," mt. J. Pept. Protein Res., 1994, 43(2), 160-5.

Kelly et al., Chemical Abstracts, 122:114965, 1994.

Kino, Toru et at., "Fk-506, A novel immunosuppressnt isolateded from A Streptomyces," J. of Antibiotics, 1987,40(9), 1249-55.

Kocienski, P. et at., "A synthesis of the C(1)-C(15) segment of tsukubaenolide (FK506)," Tetrahedron Lett., 1988, 29 (35), 4481-4.

Krit, N. A. et al., "Influence of alkyl radical on biological activity of N-carboxyalkyl dipeptides," Chemical Pharmaceutical Journal, 1991, vol. 25, No. 7, pp. 44-46.

Linde, Robert G. et al., "Straightforward synthesis of 1,2,3-tricarbonyl systems," J. Org. Chem., 1991, 56(7), 2534-8.

Luengo, J. et al., "Structure-activity studies of rapamycin analogs: evidence that the C-7 methodoxy group is part of the effector domain and positioned at the FKBP:12-FRAP interface," Chem. Biol., 1995, 2(7) 471-481.

Luengo, J. et al., "Studies on the chemistry of rapamycirt: novel transformation under Lewis-acid catalysis," Tetrahedron Lett., 1993, 34(6), 991-4.

Luengo, Juan I. et al. "Synthesis and Structure-Activity Relationships of Macrocycllc FKBP Ltgands," Bioorganic & Medicinal Chemistry Letters, 1994, vol. 4, No. 2, pp. 321-324.

Luengo, Juan I. et al., "Efficient removal of pipecolinate from rapamycin and FK506 by reaction with tetrabutylamnionium cyanide," Tetrahedron Lett., 1993, 34(29), 4599-602.

Lyons et al., "Immunosuppressant FK506 promotes neurite outgrowth in culture of PC12 cells and sensory ganglia," Proc. Natl. Acad. Sd. USA, 1994, 91, 3191-3195.

Lyons, W. Ernest et al., "Neronal Regeneration Enhances the Expression of the Immunophilin FKBP-12," The Journal of Neuroscience, 1995, 15, 2985-94.

Marshall, J.A. et al., Convenient synthesis of dioxopiperazines via aminotysis of a-(pyruvylamino) esters, Synth. Commun., 1975, 5(3), 237-44.

Mashkovskii, M.D. et al., "1-(4-(2-hydroxy-e-tert-butylaminopropoxy)indole-3-yl 95-acetamido-1-(S)-carboxypentyl)-DL-alanyl)-L-proline dihydrochloride: A new inhibitor of angiotensin converting enzyme with 13-adrenoblocking properties," Chemical Pharmaceutical Journal, 1993, vol. 27, No. 10, pp. 16-20.

Munegumi. Toratane et al., "Asymmetric Catalytic Hydrogenations of N-pyruvoyl- (S)-proline esters," Bull. Chem. Soc. Jpn., 1987, 60(1), 243-53.

Munegumi, Toratane et al., Diastereoselective Catalytic Hydrogenation of Nw~Pywvoyl~(S)~prolinamide,~ Bull. Chem. Soc. Jpn., 63:1823-34 (1990).

Munoz, Benito et al., "u-Ketoamide Phe-Pro isostere as a new core structure for the inhibition of HIV protease," Bioorg. Med. Chem., 1994, 2(10), 1085-90.

Nakatsuta, M et al. "Total Synthesis of FK506 and an FKBP Reagent, (C6, C9-C2)-FK-506," J. Am. Chem. Soc., 1990, 112 (14), 5583-90.

tNelson, F. et al., "A novel ring contraction of rapamycin," Tetrahedron Lett., 1994, 35(41), 7557-60.

Nicolaou, K.C. et al., "Total synthesis of rapanlycin," Che.-Eur. J., 1995, 1(5), 318-33.

Nicolaou, K.C. et al., "Total Synthesis of rapamycin," J. Am. Chem. Soc., 1993, 115(10), 4419-20.

Pattenden, Gerald and Tnkard, Mark, "Facile Synthesis of the tricarboriyl subunit in the immunosuppressant rapamycin," Tetrahedron Lett., 1993, 34(16), 2677-80.

Ponticelli, Claudio, "Treatment of the Nephrotic Syndrome with Cyclosporin A," J. of Autoimmunity, 1992,5,315-24.

Ranganathan, Darshan et al., "Oxalopeptldes as core motifs for protein design," J. Chem. Soc., 1993, (1), 92-4.

Ranganathan, Darshan et al., "Protein Backbone Modification by Novel Cα-C Side-Chain Scission," 1994, J. Am. Chem. Soc., 116(15), 6545-57.

Rao, A.V. Rama and Desibhatla, Vidyanand, "Studies directed towards the syntesis and rapamycin: stereoselective synthesis of C-I to C-15 segment," Tetrahedron Lett., 1993, 34(44), 7111-14.

Rao, A.V. Rama et al., "Studies directed towards the synthesis of immunosuppressive agent FK-506: synthesis of the entire bottom half," Tetrahedron Lett., 1991, 32(9), 1251-4.

Rao, A.V., et at., "Studies directed towards the synthesis of immunosuppressive agent FK-506: construction of the tricarbonyl moiety," Tetrahedron Lett., 1990, 31(10), 1439-42.

Schreiber, S.L. "Chemistry and Biology of the Immunophilins and Their Immunosuppressive Ligands," Science, 251 (1991) 283-87.

Sharkey et al., Chemical Abstracts, 121:221398, 1994.

Shu, A. et al., "Synthesis of 1-125 labeled photoaffinity rapamycin analogs," J. Labelled Compd. Radiopharm., 1996, 38(3), 277-37.

Skotnicki, Jerauld et at., "Ring expanded rapamycin derivatives," Tetrahedron Lett., 1994, 35(2), 201-2.

Skotnicki, Jerauld et al, "Synthesis of secorapamycin esters arid amides," Tetrah. Lett, 1994, 35(2), 197-200.

Slee, Deborah H. et al., Selectivity in the Inhibition of HIV and FIV Protease: Inhibitory and Mechanistic Studies of Pyrrolidine-Containing a-Keto Amide and Hydroxyethylamine Core Structures, J. Am. Chem. Soc., 1995. 117(48), 1187-78.

Smith, A.B. et at., "Total synthesis of rapamycin and demethoxyrapamycin," J. Am. Chem. Soc., 1995, 117(19), 5407-8.

Snyder. Solomon H. and Sabatini David M., "Immunophilins and the Nervous System," Nature Medicine, 1995, vol. 1, No. 1, pp. 32-37.

Soai, Kenso and Hasegawa, Hitoshi, "Diastereroselective reduction of chiral a-ketoamides derived from (S)-proline esters with sodium borohydride. Preparation of optically active a-hydroxy acids," J. Chem. Soc., 1985, 1(4), 769-72.

Soai, Kenso and Ishizaki, Miyuki, "Asymmetric Synthesis of Functionalized tertiary alcohols by diastereoselective allylation of chiral a-keto amides derived from (S)-proline esters: control of stereochemistry based on saturated coordination of Lewis acid," J. Org. Chem., 1986, 57(17) 3290-5.

Soai, Kenso and Ishizaki, Miyuki, "Disastereoselective asymmetric allylation of chiral a-keto amides with allyltrimethylsilane. Preparation of protected homoallylic alcohols," J. Chem. Soc., 1984, 15, 1016-1017.

Soai, Kenso et al., "Asymmetric Allylation of a-keto amides Derived from (S)-proline esters," Pept. Chem., 1986, 24,327-330.

Soai, Kenso et al., "Asymmetric synthesis of both eaniomers of a-hydroxy acids by the diastereoselective reduction of chiral a-keto amides with complex metal hydrides in the presence of a metal salt," Chem. Lett, 1986, 11, 1897-900.

Soai, Kenso et al., "Sodium borohydnde as diastereoselective reducing agent of chiral a-keto amides," Pept. Chem., 1982, 20, 81-4.

Soai, Kenso et al., "Unusual effect of a mixed solvent on the asymmetric reduction of chiral a-keto amides with sodium borohydride," J. Chem. Soc., 1982, 21, 1282-3.

Steffan, Robert J. et al., "Base catalyzed degradations of rapamycin," Tetrahedron Lett., 1993, 34(23), 3699-702.

Steglich Wolfgang and Hirize, Sabine, "A rationale synthesis of N-trifluroacetylamino acids," Synthesis, 1976, 8, 399-401. (German).

Steglich, Wolfgang et al., "Activated carboxylic acid derivatives. II. A simple synthesis of 2-oxycarboxytic acid amides, N-(2-oxoacyl)amino acid esters and 2-oxocarboxylic acid hydrazldes," Synthesis, 1978, 8, 622-4. (German).

Steiner, J.P. et al. "Nonimmunosuppressive Ligands for Neuroimmunophilins Promote Nerve Extension In Vitro and In Vivo," Society for Neuroscience Abstracts, 1996, 22, 297.13.

Steiner, Joseph P. et al., "High brain densities of the immunophilin FKBP colocalized with calcineunn," Nature Lett., 1992, 358, 584-7.

Stocks, M. et al., "Macrocyclic ring closures employing the intramolecular Heck reaction," Tetrahedron Lett., 1995. 36(36), 6555-8.

Stocks, M. et al., "The contribution to the binding of the pyranoside substitutents in the excised binding domain of FK-506," Bioorg. Med. Chem. Lett., 1994, 4(12), 1457-60.

Stocks, Michael J. et al. "The Contribution to Binding of the Pyranoside Substitutents in the Excised Binding Domain of DK-506," Bioorganic & Medicinal Chemistry Letters, 1994, vol. 4, No. 12, pp. 1457-1460.

Tanaka, H. et al., "Structure of FK506, a novel imunosuppressant isolated from Streptomyces," J. Am. Chem. Soc., 1987, 109(16), 5031-3.

Tatlock, J. et al., "High affinity FKBP-12 ligands from (R)-(–)-carvone. Synthesis and evaluation of FK506 pyranose ring replacements," Bioorg. Med. Chem. Lett., 1995, 5(21), 2489-94.

league, S. et al., "Synthesis of FK506-cyclosporin hybrid macrocycles," Bioorg. Med. Chem. Lett., 1995, 5(20), 2341-6.

Teague, Simon J. et al. "Synthesis and Study of a Non Macrocyclic FK506 Derivative," Bioorganic & Medical Chemistry Letters, 1994, vol. 4, No. 13, pp. 1581-1584.

Teague, Simon J. et al. "The Affinity of the Excised Binding Domain of FK-506 for the Immunophilin FKBPI2," Bioorganic & Medicinal Chemistry Letters, 1993. vol. 3, No. 10, pp. 1947-1950.

Tindall, Richard S.A., "Immunointervention with Cyciosporin A in utoimmune Neurological Disorders," J. of Autoimmunity, 1992, 5, 301-13.

Tugwell, Peter, "Clyclosporin in the Treatment of Rheumatoid Arthritis," J. of Autolmmunity, 1992, 5, 231-40.

Waldmann, Herbert, "Amino acid esters as chiral auxiliaries in Battier-type reactions in aqueous solutions," Liebigs Ann. Chem., 1991, (12), 131 7-22.

Waldmann, Herbert, "Proline Benzyl Ester as Chiral Auxiliary in Barbier-Type Reactions in Aqueous Solution," Synlett Left. 10: 627-28 (1990).

Wang, C.P. et al., "A high performance liquid chromatographic method for the determination of rapamycin {sirolimus} in rat serum, plasma, and blood and in monkey serum," J. Liq. Chromatogr., 1995, 18(9), 1801-8.

Wang C.P. et al., "High performance liquid chromatographic isolation and spectroscopic characterization of three major metabolites from the plasma of rats receiving raparnycin {sirolimus} orally," J. Liq. Chromatogr., 1995, 18(13), 2559-68.

Wang, Gary T. et al. "Synthesis and FKBP Binding of Small Molecule Mimics of the Tricarbonyl Region of FK506," Bioorganic & Medicinal Chemistry Letters, 1994, vol. 4, No. 9, pp. 1161-1166.

Wasserman, H.H. et al.,"Synthesis of the tncarbonyl region of FK-506 through and amidophosphorane (Erratum to document cited in CA1I1(7) :57366pJ," J. Org. Chem., 1989, 54(22), 5406.

Wasserman, H.H. et al., "Synthesis of the tricarbonyl region of FK-506 through an amidosphere," J. Org. Chem., 1989. 54(12), 2785-6.

Whitesell, J.K. et al., "Asymmetric Induction. Reduction, Nucleophilic Addition to, Ene Reactions of Chiral α-Ketoesters," J. Chem. Soc., Chem Commun., 1983, 802.

Williams, D.R. and Benbow, J.W., "Synthesis of the a,~3 diketo amide segment of the novel immunosuppressive FK506," J. Org. Chem., 1988, 53(191), 4643-4.

Yamamoto, Satoshi et al. "Stimulation of Hair Growth by Topical Application of FK506, a Potent Immunosuppressive Agent," J. Invest. Dermatol., (1994) 102:2, 160-64.

Yamashita, Dennis S. et al. "Design Synthesis and Evaluation of Dual Domain FKBP Ligands," Bioorganic & Medicinal Chemistry Letters, 1994, vol. 4. No. 2, pp. 325-328.

Yohannes, Daniel et al., "Degradation of rapamycin: retrieval of major intact subunits," Tetrahedron Left., 1992, 33 (49), 7469-72.

Yohannes, Daniel et al., "Degradation of rapamycin: synthesis of a rapamycin-derived fragment containing the tncarbonyl and triene sectors," Tetrahedron Lett., 1993, 34(13), 2075-8.

SMALL MOLECULE INHIBITORS OF ROTAMASE ENZYME ACTIVITY

This application is a continuation of application Ser. No. 11/871,358, filed Oct. 12, 2007, now U.S. Pat. No. 7,652,060 which application is a continuation of application Ser. No. 11/166,220, filed Jun. 27, 2005, now U.S. Pat. No. 7,282,510 which application is a divisional of application Ser. No. 10/219,887 filed Aug. 16, 2002, now abandoned, which application is a continuation of application Ser. No. 09/605,475 filed Jun. 28, 2000, now U.S. Pat. No. 6,500,959, which application is a continuation of application Ser. No. 08/833,629 filed Apr. 8, 1997, now U.S. Pat. No. 6,140,357, which application is a continuation of application Ser. No. 08/650,461 filed May 21, 1996, now U.S. Pat. No. 5,859,031, which application is a continuation-in-part of application Ser. No. 08/479,436 filed, Jun. 7, 1995, now U.S. Pat. No. 5,614,547; each of which is explicitly incorporated by reference.

BACKGROUND OF THE INVENTION

1. Field of the Invention

This invention relates to neurotrophic compounds having an affinity for FKBP-type immunophilins, their preparation and use as inhibitors of the enzyme activity associated with immunophilin proteins, and particularly inhibitors of peptidyl-prolyl isomerase or rotamase enzyme activity.

2. Description of the Prior Art

The term immunophilin refers to a number of proteins that serve as receptors for the principal immunosuppressant drugs, cyclosporin A (CsA), FK506, and rapamycin. Known classes of immunophilins are cyclophilins, and FK506 binding proteins, such as FKBP. Cyclosporin A binds to cyclophilin while FK506 and rapamycin bind to FKBP. These immunophilin-drug complexes interface with a variety of intracellular signal transduction systems, especially in the immune system and the nervous system.

Immunophilins are known to have peptidyl-prolyl isomerase (PPIase) or rotamase enzyme activity. It has been determined that rotamase activity has a role in the catalyzation of the interconversion of the cis and trans isomer of immunophilin proteins.

Immunophilins were originally discovered and studied in immune tissue. It was initially postulated by those skilled in the art that inhibition of the immunophilins rotamase activity leads to the inhibition of T-cell proliferation, thereby causing the immunosuppressive action exhibited by immunosuppressive drugs such as cyclosporin A, FK506, and rapamycin. Further study has shown that the inhibition of rotamase activity, in and of itself, is not sufficient for immunosuppressant activity. Schreiber et al., Science, 1990 vol. 250 pp. 556-559. It has been shown that the immunophilin-drug complexes interact with ternary protein targets as their mode of action. Schreiber et al., Cell, 1991, vol. 66, pp. 807-815. In the case of FKBP-FK506 and FKBP-CsA, the drug-immunophilin complexes bind to the enzyme calcineurin, inhibitory T-cell receptor signalling leading to T-cell proliferation. Similarly, the complex of rapamycin and FKBP interacts With the RAFTI/FRAP protein and inhibits signalling from the IL-2 receptor.

Immunophilins have been found to be present at high concentrations in the central nervous system. Immunophilins are enriched 10-50 times more in the central nervous system than in the immune system. Within neural tissues, immunophilins appear to influence neuronal process extension, nitric oxide synthesis, and neurotransmitter release.

It has been found that picomolar concentrations of an immunosuppressant such as FK506 and rapamycin stimulate neurite out growth in PC12 cells and sensory nervous, namely dorsal root ganglion cells (DRGs). Lyons et al., Proc. of Natl. Acad. Sci., 1994 vol. 91, pp. 3191-3195. In whole animal experiments, FK506 has been shown to stimulate nerve regeneration following facial nerve injury and results in functional recovery in animals with sciatic nerve lesions.

Surprisingly, it has been found that drugs with a high affinity for FKBP are potent rotamase inhibitors causing a neurotrophic effect. Lyons et al. These findings suggest the use of immunosuppressants in treating various peripheral neuropathies and enhancing neuronal regrowth in the central nervous system (CNS). Studies have demonstrated that neurodegenerative disorders such as Alzheimer's disease, Parkinson's disease, and amyotrophic lateral sclerosis (ALS) may occur due to the loss, or decreased availability, of a neurotrophic substance specific for a particular population of neurons affected in the disorder.

Several neurotrophic factors effecting specific neuronal populations in the central nervous system have been identified. For example, it has been hypothesized that Alzheimer's disease results from a decrease or loss of nerve growth factor (NGF). It has thus been proposed to treat Alzheimer's patients with exogenous nerve growth factor or other neurotrophic proteins such as brain derived nerve factor (BDNF), glial derived nerve factor, ciliary neurotrophic factor, and neurotropin-3 to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentially serious side effects including nephrotoxicity, such as impairment of glomerular filtration and irreversible interstitial fibrosis (Kopp et al., 1991, *J. Am. Soc. Nephrol.* 1:162); neurological deficits, such as involuntary tremors, or non-specific cerebral angina such as non-localized headaches (De Groen et al., 1987, *N. Engl. J. Med.* 317:861); and vascular hypertension with complications resulting therefrom (Kahan et al., 1989 *N. Engl. J, Med.* 321:1725).

In order to prevent the side effects associated with use of the immunosuppressant compounds, the present invention provides nonimmunosuppressive compounds containing small molecule FKBP rotamase inhibitors for promoting neuronal growth and regeneration in various neuropathological situations where neuronal repair can be facilitated including peripheral nerve damage by physical injury or disease state such as diabetes, physical damage to the central nervous system (spinal cord and brain) brain damage associated with stroke, and for the treatment of neurological disorders relating to neurodegeneration, including Parkinson's disease, Alzheimer's disease, and amyotrophic lateral sclerosis.

SUMMARY OF THE INVENTION

The present invention relates to a novel class of neurotrophic compounds having an affinity for FKBP-type immunophilins. Once bound to this protein the neurotrophic compounds are potent inhibitors of the enzyme activity associated with immunophilin proteins and particularly rotamase enzyme activity, thereby stimulating neuronal regeneration and outgrowth. A key feature of the compounds of the present invention is that they do not exert any significant immunosuppressive activity in addition to their neurotrophic activity.

A preferred embodiment of this invention is a neurotrophic compound of the formula:

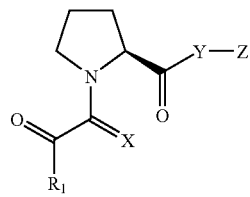

where $R_1$ is selected from the group consisting of a $C_1$-$C_9$ straight or branched chain alkyl or alkenyl group optionally substituted with $C_3$-$C_8$ cycloalkyl, $C_3$ or $C_5$ cycloalkyl, $C_5$-$C_7$ cycloalkenyl, $Ar_1$, where said alkyl, alkenyl, cycloalkyl or cycloalkenyl groups may be optionally substituted with $C_1$-$C_4$ alkyl, $C_1$-$C_4$ alkenyl, or hydroxy, where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-, 3-, 4-pyridyl, and phenyl, having one to three substituents which are independently selected from the group consisting of hydrogen, halo, hydroxyl, nitro, trifluoromethyl, $C_1$-$C_6$ straight or branched alkyl or alkenyl, $C_1$-$C_4$ alkoxy or $C_1$-$C_4$ alkenyloxy, phenoxy, benzyloxy, and amino;

X is selected from the group consisting of oxygen, sulfur, methylene ($CH_2$), or $H_2$;

Y is selected from the group consisting of oxygen or $NR_2$, where $R_2$ is hydrogen or $C_1$-$C_6$ alkyl; and Z is selected from the group consisting of $C_2$-$C_6$ straight or branched, chain alkyl or alkenyl, wherein the alkyl chain is substituted in one or more positions with $Ar_1$ as defined above, $C_3$-$C_8$ cycloalkyl, cycloalkyl connected by a $C_1$-$C_6$ straight or unbranched alkyl or alkenyl chain, and $Ar_2$ where $Ar_2$ is selected from the group consisting of 2-indolyl, 3-indolyl, 2-furyl, 3-furyl, 2-thiazolyl, 2-thienyl, 3-thienyl, 2,3-, or 4-pyridyl, and phenyl, having one to three substituents which are independently selected from the group consisting of hydrogen, halo, hydroxyl, nitro, trifluoromethyl, $C_1$-$C_6$ straight or branched alkyl or alkenyl, $C_1$-$C_4$ alkoxy or $C_1$-$C_4$ alkenyloxy, phenoxy, benzyloxy, and amino;

Z may also be the fragment:

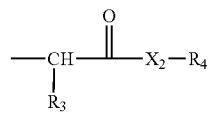

where $R_3$ is selected from the group consisting of straight or branched alkyl $C_1$-$C_8$ optionally substituted with $C_3$-$C_8$ cycloalkyl, or $Ar_1$ as defined above, and unsubstituted $Ar_1$;

$X_2$ is O or $NR_S$, where $R_5$ is selected from the group consisting of hydrogen, $C_1$-$C_6$ straight or branched alkyl and alkenyl;

$R_4$ is selected from the group consisting of phenyl, benzyl, $C_1$-$C_5$ straight or branched alkyl or alkenyl, and $C_1$-$C_5$ straight or branched alkyl or alkenyl substituted with phenyl; or pharmaceutically acceptable salts or hydrates thereof.

Another preferred embodiment of this invention is a neurotrophic compound of the formula:

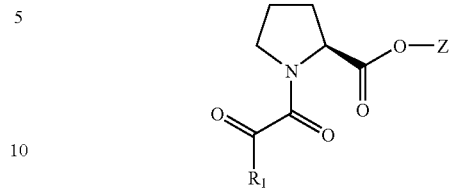

where $R_1$ is a $C_1$-$C_9$ straight or branched chain alkyl or alkenyl group optionally substituted with $C_3$-$C_8$ cycloalkyl, $C_3$ or $C_5$ cycloalkyl, $C_5$-$C_7$ cycloalkenyl, or $Ar_1$, where said alkyl, alkenyl, cycloalkyl or cycloalkenyl groups may be optionally substituted with $C_1$-$C_4$ alkyl, $C_1$-$C_4$ alkenyl, or hydroxy, and where $Ar_1$ is selected from the group consisting of L-naphthyl, 2-naphthyl, 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$-$C_6$ straight or branched alkyl or alkenyl, $C_1$-$C_4$ alkoxy or $C_1$-$C_4$ alkenyloxy, phenoxy, benzyloxy, and amino;

Z is a $C_2$-$C_6$ straight or branched chain alkyl or alkenyl, wherein the alkyl chain is substituted in one or more positions with $Ar_1$ as defined above, $C_3$-$C_8$ cycloalkyl, cycloalkyl connected by a $C_1$-$C_6$ straight or unbranched alkyl or alkenyl chain, or $Ar_2$ where $Ar_2$ is selected from the group consisting of 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, $C_1$-$C_6$ straight or branched alkyl or alkenyl, $C_1$-$C_4$ alkoxy or $C_1$-$C_4$ alkenyloxy, phenoxy, benzyloxy, and amino; or pharmaceutically acceptable salts or hydrates thereof.

Another preferred embodiment of this invention is a neurotrophic compound of the formula:

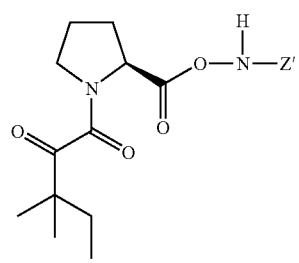

where Z' is the fragment:

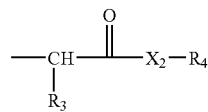

where $R_3$ is selected from the group consisting of straight or branched alkyl $C_1$-$C_8$ optionally substituted with $C_3$-$C_8$ cycloalkyl, or $Ar_1$ as defined above, and unsubstituted $Ar_1$;

$X_2$ is O or $NR_S$, where $R_5$ is selected from the group consisting of hydrogen, $C_1$-$C_6$ straight or branched alkyl and alkenyl;

R$_4$ is selected from the group consisting of phenyl, benzyl, C$_1$-C$_5$ straight or branched alkyl or alkenyl, and C$_1$-C$_5$ straight or branched alkyl or alkenyl substituted with phenyl; or pharmaceutically acceptable salts or hydrates thereof.

Another preferred embodiment of the invention is a neurotrophic compound having an affinity for FKBP-type immunophilins which inhibit the rotamase activity of the immunophilin.

Another preferred embodiment of the present invention is a method for treating a neurological disorder in an animal comprising administering a therapeutically effective amount of a compound having an affinity for FKBP-type immunophilins which inhibits the rotamase activity of the immunophilin.

Another preferred embodiment of the invention is a method of promoting neuronal regeneration and growth in mammals, comprising administering to a mammal an effective amount of a neurotrophic compound having an affinity for FKBP-type immunophilins which inhibits the rotamase activity of the immunophilin.

Yet another preferred embodiment of the invention is a method of preventing neurodegeneration in an animal comprising administering to an animal an effective amount of a neurotrophic compound having an affinity for FKBP-type immunophilins which inhibits rotamase activity of the immunophilin.

DETAILED DESCRIPTION OF THE INVENTION

The novel neurotrophic compounds of this invention are relatively small molecules in relation to other known compounds which bind to FKBP-type immunophilins, such as rapamycin, FK506, and cyclosporin.

The neurotrophic compounds of this invention have an affinity for the FKS06 binding proteins such as FKBP-12. When the neurotrophic compounds of the invention are bound to the FKBP, they have been found to unexpectedly inhibit the prolyl-peptidyl cis-trans isomerase activity, or rotamase activity of the binding protein and stimulate neurite growth, while not exhibiting an immunosuppressant effect. More particularly, this invention relates to a novel class of neurotrophic compounds represented by the formula:

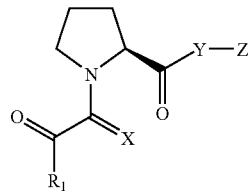

where R$_1$ is a C$_1$-C$_9$ straight or branched chain alkyl or alkenyl group optionally substituted with C$_3$-C$_8$ cycloalkyl, C$_3$ or C$_5$ cycloalkyl, C$_5$-C$_7$ cycloalkenyl, or Ar$_1$, where said alkyl, alkenyl, cycloalkyl or cycloalkenyl groups may be optionally substituted with C$_1$-C$_4$ alkyl, C$_1$-C$_4$ alkenyl, or hydroxy, and where Ar$_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, C$_1$-C$_6$ straight or branched alkyl or alkenyl, C$_1$-C$_4$ alkoxy or C$_1$-C$_4$ alkenyloxy, phenoxy, benzyloxy, and amino;

X is oxygen, sulfur, methylene (CH$_2$), or H$_2$;

Y is oxygen or NR$_2$, where R$_2$ is hydrogen or C$_1$-C$_6$ alkyl; and

Z is a C$_1$-C$_6$ straight or branched chain alkyl or alkenyl, wherein the alkyl chain is substituted in one or more positions with Ar$_1$ as defined above, C$_3$-C$_8$ cycloalkyl, cycloalkyl connected by a C$_1$-C$_6$ straight or unbranched alkyl or alkenyl chain, or Ar$_2$ where Ar$_2$ is selected from the group consisting of 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, C$_1$-C$_6$ straight or branched alkyl or alkenyl, C$_1$-C$_4$ alkoxy or C$_1$-C$_4$ alkenyloxy, phenoxy, benzyloxy, and amino;

Z may also be the fragment:

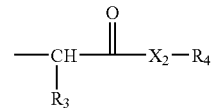

where

R$_3$ is selected from the group consisting of straight or branched alkyl C$_1$-C$_8$ optionally substituted with C$_3$-C$_8$ cycloalkyl, or Ar$_1$ as defined above, and unsubstituted Ar$_1$;

X$_2$ is O or NR$_S$, where R$_5$ is selected from the group consisting of hydrogen, C$_1$-C$_6$ straight or branched alkyl and alkenyl;

R$_4$ is selected from the group consisting of phenyl, benzyl, C$_1$-C$_5$ straight or branched alkyl or alkenyl, and C$_1$-C$_5$ straight or branched alkyl or alkenyl substituted with phenyl; or pharmaceutically acceptable salts or hydrates thereof.

Preferred compounds have the following formula:

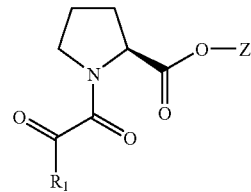

where

R$_1$ is a C$_1$-C$_9$ straight or branched chain alkyl or alkenyl group optionally substituted with C$_3$-C$_8$ cycloalkyl, C$_3$ or C$_5$ cycloalkyl, C$_5$-C$_7$ cycloalkenyl, or Ar$_1$, where said alkyl, alkenyl, cycloalkyl or cycloalkenyl groups may be optionally substituted with C$_1$-C$_4$ alkyl, C$_1$-C$_4$ alkenyl, or hydroxy, and where Ar$_1$ is selected from the group consisting of 1naphthyl, 2-naphthyl, 2-indolyl, 3-indolyl, 2-furyl, 3-furyl, 2-thiazolyl, 2-thienyl, 3-thienyl, 2-, 3-, or 4-pyridyl, or phenyl, having one to three substituents which are independently selected from the group consisting of hydrogen, halo, hydroxyl, nitro, trifluoromethyl, C$_1$-C$_6$ straight or branched alkyl or alkenyl, C$_1$-C$_4$ alkoxy or C$_1$-C$_4$ alkenyloxy, phenoxy, benzyloxy, and amino;

Z is a C$_2$-C$_6$ straight or branched chain alkyl or alkenyl, wherein the alkyl chain is substituted in one or more positions with Ar$_1$ as defined above, C$_3$-C$_8$ cycloalkyl, cycloalkyl connected by a C$_1$-C$_6$ straight or unbranched alkyl or alkenyl chain, or Ar$_2$ where Ar$_2$ is selected from the group consisting of 2-indolyl, 3-indolyl, 2-furyl, 3-furyl, 2-thiazolyl, 2-thienyl, 3-thienyl, 2-, 3-, or 4pyridyl, or phenyl, having one to three substituents which are independently selected from the group consisting of hydrogen, halo, hydroxyl, nitro, trifluoromethyl, $C_1$-$C_6$ straight or branched alkyl or alkenyl, $C_1$-$C_4$ alkoxy or $C_1$-$C_4$ alkenyloxy, phenoxy, benzyloxy, and amino; or pharmaceutically acceptable salts or hydrates thereof.

In another preferred embodiment novel compounds of this invention are represented by the formula:

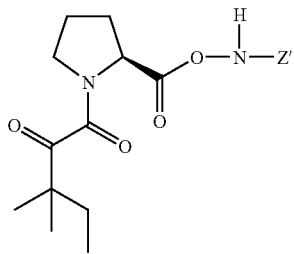

where

Z' is the fragment:

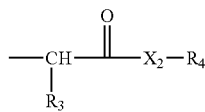

where $R_3$ is selected from the group consisting of straight or branched alkyl $C_1$-$C_8$ optionally substituted with $C_3$-$C_8$ cycloalkyl, or $Ar_1$ as defined above, or unsubstituted $Ar_1$;

$X_2$ is O or $NR_5$, where $R_5$ is selected from the group consisting of hydrogen, $C_1$-$C_6$ straight or branched alkyl and alkenyl;

$R_4$ is selected from the group consisting of phenyl, benzyl, $C_1$-$C_5$ straight or branched alkyl or alkenyl, and $C_1$-$C_5$ straight or branched alkyl or alkenyl substituted with phenyl; or pharmaceutically acceptable salts or hydrates thereof.

The compounds of this invention exist as stereoisomeric forms, either enantiomers or diastereoisomers. The stereochemistry at position 1 (Formula 1) is R or S, with S preferred. Included within the scope of the invention are the enantiomers, the racemic form, and diastereoisomeric mixtures. Enantiomers as well as diastereoisomers can be separated by methods known to those skilled in the art.

It is known that immunophilins such as FKBP preferentially recognize peptide substrates containing Xaa-Pro-Yaa motifs, where Xaa and Yaa are lipophilic amino acid residues. Schreiber et al. 1990 J. Org. Chem. 55, 4984-4986; Harrison and Stein, 1990 Biochemistry, 29, 3813-3816. Thus modified prolyl peptidomimetic compounds bearing lipophilic substituents should bind with high affinity to the hydrophobic core of the FKBP active site and inhibit its rotamase activity.

Preferred compounds of the invention include:
3-phenyl-1-propyl (2S)-1-(3,3-dimethyl-1,2-dioxopentyl)-2-pyrrolidinecarboxylate,
3-phenyl-1-prop-2-(E)-enyl (2S)-1-(3,3-dimethyl-1,2-dioxopentyl)-2-pyrrolidinecarboxylate,
3-(3,4,S-trimethoxyphenyl)-1-propyl (2S)-1-(3,3-dimethyl-1,2-dioxopentyl)-2-pyrrolidinecarboxylate,
3-(3,4,S-trimethoxyphenyl)-1-prop-2-(E)-enyl (2S)-1-(3,3-dimethyl-1,2-dioxopentyl)-2-pyrrolidinecarboxylate,
3-(4,S-dichlorophenyl)-1-propyl (2S)-1-(3,3-dimethyl-1,2-dioxopentyl)-2-pyrrolidinecarboxylate,
3-(4,S-dichlorophenyl)-1-prop-2-(E)-enyl (2S)-1-(3,3-dimethyl-1,2-dioxopentyl)-2-pyrrolidinecarboxylate,
3~(4,5-methylenedioxyphenyl)-1-propyl (2S)-1-(3,3-dimethyl-1,2-dioxopentyl)-2-pyrrolidinecarboxylate,
3-(4,5-methylenedioxyphenyl)-1-prop-2-(E)-enyl (2S)-1-(3, 3-dimethyl-1,2-dioxopentyl)-2-pyrrolidinecarboxylate,
3-cyclohexyl-1-propyl (2S)-1-(3,3-dimethyl-1,2-dioxopentyl)-2-pyrrolidinecarboxylate,
3-cyclohexyl-1-prop-2-(E)-enyl (2S)-1-(3,3-dimethyl-1,2-dioxopentyl)-2-pyrrolidinecarboxylate,
(1R)-1,3-diphenyl-1-propyl (2S)-1-(3,3-dimethyl-1,2-dioxopentyl)-2-pyrrolidinecarboxylate,
(1R)-1,3-diphenyl-1-prop-2-(E)-enyl (2S)-1-(3,3-dimethyl-1,2-dioxopentyl)-2-pyrrolidinecarboxylate,
(1R)-1-cyclohexyl-3-phenyl-1-propyl (2S)-1-(3,3-dimethyl-1,2-dioxopentyl)-2-pyrrolidinecarboxylate,
(1R)-1-cyclohexyl-3-phenyl-1-prop-2-(E)-enyl (2S)-1-(3,3-dimethyl-1,2-dioxopentyl)-2-pyrrolidinecarboxylate,
(1R)-1-(4,S-dichlorophenyl)-3-phenyl-1-propyl (2S)-1-(3,3-dimethyl-1,2-dioxopentyl)-2-pyrrolidinecarboxylate,
3-phenyl-1-propyl (2S)-1-(1,2-dioxo-2-cyclohexyl)ethyl-2-pyrrolidinecarboxylate,
3-phenyl-1-propyl (ZS)-1-(1,Z-dioxo-4-cyclohexyl)butyl-2-pyrrolidinecarboxylate,
3-phenyl-1-propyl (2S)-1-(1,2-dioxo-2[Z-furanylDethyl-2-pyrrolidinecarboxylate,
3-phenyl-1-propyl (ZS)-1-(1,Z-dioxo-2[2-thienylDethyl-2-pyrrolidinecarboxylate,
3-phenyl-1-propyl (2S)-1-(1,2-dioxo-2-[2-thiazolylDethyl-2-pyrrolidinecarboxylate,
3-phenyl-1-propyl (2S)-1-(1,2-dioxo-2-phenyl)ethyl-2-pyrrolidinecarboxylate,
1,7-diphenyl-4-heptyl (2S)-1-(3,3-dimethyl-1,Z-dioxopentyl)-2-pyrrolidinecarboxylate,
3-Phenyl-1-propyl (2S)-1-(3,3-dimethyl-1,2-dioxo-4-hydroxybutyl)-2-pyrrolidinecarboxylate,
3-phenyl-1-propyl (2S)-1-(3,3-dimethyl-1,2-dioxopentyl)-2pyrrolidinecarboxamide,
1-[1-(3,3-dimethyl-1,2-dioxopentyl)-L-proline]-L-phenylalanine ethyl ester,
1-[1-(3,3-dimethyl-1,2-dioxopentyl)-L-proline]-L-leucine ethyl ester,
1-[1-(3,3-dimethyl-1,2-dioxopentyl)-L-proline]-L-phenylglycine ethyl ester,
1-[1-(3,3-dimethyl-1,2-dioxopentyl)-L-proline]-L-phenylalanine phenyl ester,
1-[1-(3,3-dimethyl-1,2-dioxopentyl)-L-proline]-L-phenylalanine benzyl ester, and
1(1-(3,3-dimethyl-1,2-dioxopentyl)-L-proline]-L-isoleucine ethyl ester.

The compounds of the present invention can be used in the form of salts derived from inorganic or organic acids and bases. Included among such acid salts are the following: acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, propionate, succinate, tartrate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The neurotrophic compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to mammals other than humans for treatment of various mammalian neurological disorders.

The novel compounds of the present invention are potent inhibitors of rotamase activity and possess an excellent degree of neurotrophic activity. This activity is useful in the stimulation of damaged neurons, the promotion of neuronal regeneration, the prevention of neurodegeneration, and in the treatment of several neurological disorders known to be associated with neuronal degeneration and peripheral neuropathies. The neurological disorders that may be treated include but are not limited to: trigeminal neuralgia, glossopharyngeal neuralgia, Bell's Palsy, myasthenia gravis, muscular dystrophy, amyotrophic lateral sclerosis, progressive muscular atrophy, progressive bulbar inherited muscular atrophy, herniated, ruptured or prolapsed invertabrae disk syndromes, cervical spondylosis, plexus disorders, thoracic outlet destruction syndromes, peripheral neuropathic such as those caused by lead, dapsone, ticks, prophyria, or Gullain-Barre syndrome, Alzheimer's disease, and Parkinson's disease.

For these purposes the compounds of the present invention may be administered orally, parenterally, by inhalation spray, topically, rectally, nasally, buccally, vaginally or via an implanted reservoir in dosage formulations containing conventional non-toxic pharmaceutically acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets the immunophilin-drug complex should readily penetrate the blood-brain barrier when peripherally administered. Compounds of this invention which cannot penetrate the blood-brain barrier can be effectively administered by an intraventricular route.

The pharmaceutical compositions may be in the form of a sterile injectable preparation, for example as a sterile injectable aqueous or oleaginous suspension. This suspension may be formulated according to techniques know in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. Fatty acids such as oleic acid and its glyceride derivatives find use in the preparation of injectables, olive oil or castor oil, especially in their polyoxyethylated versions. These oil solutions or suspensions may also contain a long-chain alcohol diluent or dispersant.

The compounds may be administered orally in the form of capsules or tablets, for example, or as an aqueous suspension or solution. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening and/or flavoring and/or coloring agents may be added.

The compounds of this invention may also be administered in the form of suppositories for rectal administration of the drug. These compositions can be prepared by mixing the drug with a suitable non-irritating excipient which is solid at room temperature but liquid at rectal temperature and therefore will melt in the rectum to release the drug. Such materials include cocoa butter, beeswax and polyethylene glycols.

The compounds of this invention may also be administered optically, especially when the conditions addressed for treatment involve areas or organs readily accessible by topical application, including neurological disorders of the eye, the skin, or the lower intestinal tract. Suitable topical formulations are readily prepared for each of these areas.

For ophthalmic use, the compounds can be formulated as micronized suspensions in isotonic, pH adjusted sterile saline, or, preferably, as solutions is isotonic, pH adjusted sterile saline, either with or without a preservative such as benzylalkonium chloride. Alternatively for the ophthalmic uses the compounds may be formulated in an ointment such as petrolatum.

For application topically to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract can be effected in a rectal suppository formulation (see above) or in a suitable enema formulation.

Dosage levels on the order of about 0.1 mg to about 10,000 mg. of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

$K_i$ Test Procedure

Inhibition of the peptidyl-prolyl isomerase (rotamase) activity of the inventive compounds can be evaluated by known methods described in the literature (Harding, M. W. et al. *Nature* 341:758-760 (1989); Holt et al. *J. Am. Chem. Soc.* 115: 9923-9938). These values are obtained as apparent $K_i$'s and are presented for some of Examples 1-30 in Table 1. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent $K_i$ values.

In a plastic cuvette are added 950 mL of ice cold assay buffer (25 mM HEPES, pH 7.8, 100 mM NaCl), 10 mL of FKBP (2.5 mM in 10 mM TrisCl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 sec using a spectrophotometer and the rate constants are determined from the absorbance versus time data files.

The data for these experiments is presented in Table I.

TABLE I

| FKBP ROTAMASE INHIBITION | |
|---|---|
| Example | Ki nM |
| 4 | 42 |
| 5 | 125 |
| 6 | 200 |
| 7 | 65 |
| 8 | 2500 |
| 9 | 160 |
| 10 | 52 |
| 24 | 9000 |

In mammalian cells, FKBP-12 complexes with the inositol triphosphate receptor ($IP_3R$) and the ryanodine receptor (RyR). It is believed that the neurotrophic compounds of this invention disassociates FKBP-12 from these complexes causing the calcium channel to become "leaky" (Cameron et al., 1995). Calcium fluxes are involved in neurite extensions so that the $IP_3R$ receptor and the ryanodine receptor might be involved in the neurotrophic effects of drugs. Since the drugs bind to the same site as FKBP-12 as the $IP_3R$ receptor, one could assume that the drugs displace the channels from FKBP-12.

Chick Dorsal Root Ganglion Cultures and Neurite Outgrowth

Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 μM cytosine β-D arabinofuranoside (Ara C) at 37° C. in an environment containing 5% $CO_2$. Twenty-four hours later, the DRGs were treated with various concentrations of nerve growth factor, immunophilin ligands or combinations of NFG plus drugs. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate. The data for these experiments are presented in Table II.

TABLE II

| Neurite Outgrowth in Chick DRG | |
|---|---|
| Example | ED50 (nM) |
| 4 | 53 |
| 5 | 105 |
| 6 | 149 |
| 7 | 190 |
| 8 | 850 |
| 9 | 75 |
| 10 | — |
| 24 | — |

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLES

The inventive compounds may be prepared by a variety of synthetic sequences that utilize established chemical transformations. The general pathway to the present compounds is described in Scheme I. N-glyoxylproline derivatives may be prepared by reacting L-proline methyl ester with methyl oxalyl chloride as shown in Scheme I. The resulting oxamates may be reacted with a variety of carbon nucleophiles to obtain intermediates compounds. These intermediates are then reacted with a variety of alcohols, amides, or protected amino acid residues to obtain the propyl esters and amides of the invention.

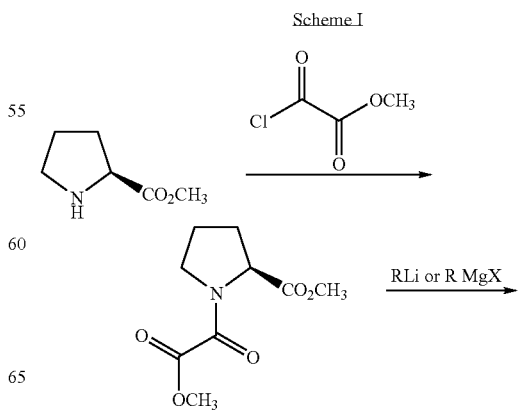

Scheme I

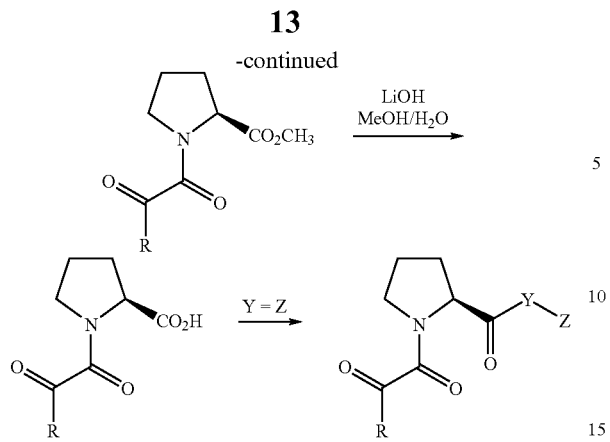

Example 1

Synthesis of methyl (2S)-1-(1,2-dioxo-2-methoxy-ethyl)-2-pyrrolidinecarboxylate

A solution of L-proline methyl ester hydrochloride (3.08 g; 18.60 mmol) in dry methylene chloride was cooled to 0° C. and treated with triethylamine (3.92 g; 38.74 mmol; 2.1 eq). After stirring the formed slurry under a nitrogen atmosphere for 15 min) a solution of methyl oxalyl chloride (3.20 g; 26.12 mmol) in methylene chloride (45 mL) was added dropwise. The resulting mixture was stirred at 0° C. for 1.5 hr. After filtering to remove solids, the organic phase was washed with water, dried over $MgSO_4$ and concentrated. The crude residue was purified on a silica gel column, eluting with 50% ethyl acetate in hexane, to obtain 3.52 g (88%) of the product as a reddish oil. Mixture of cis-trans amide rotamers; data for trans rotamer given. $^1$HNMR ($CDCl_3$): d 1.93 (dm, 2H); 2.17 (m, 2H); 3.62 (m, 2H); 3.71 (s, 3H); 3.79, 3.84 (s, 3H total); 4.86 (dd, 1H, J=8.4, 3.3).

Example 2

General procedure for the synthesis of pyrrolidinyl alkyl oxamates. Exemplified for methyl (2S)-1-(1,2-dioxo-3,3-dimethylpentyl)-2-pyrrolidinecarboxylate.

A solution of methyl (2S)-1-(1,2-dioxo-2-methoxyethyl)-2-pyrrolidinecarboxylate (2.35 g; 10.90 mmol) in 30 mL of tetrahydrofuran (THF) was cooled to −78° C. and treated with 14.2 mL of a 1.0 M solution of 1,1-dimethylpropylmagnesium chloride in THF. After stirring the resulting homogeneous mixture at −78° C. for three hours, the mixture was poured into saturated ammonium chloride (100 mL) and extracted into ethyl acetate. The organic phase was washed with water, dried, and concentrated, and the crude material obtained upon removal of the solvent was purified on a silica gel column, eluting with 25% ethyl acetate in hexane, to obtain 2.10 g (75%) of the oxamate as a colorless oil. $^1$HNMR ($CDCl_3$): d 0.88 (t, 3H); 1.22, 1.26 (5, 3H each); 1.75 (dm, 2H); 1.87-2.10 (m, 3H); 2.23 (m, 1H); 3.54 (m, 2H); 3.76 (s, 3H); 4.52 (dm, 1H, J=8.4, 3.4).

Example 3

General procedure for the preparation of pyrrolidine carboxylic acids. Exemplified for (2S)-1-(1,2-dioxo-3,3-dimethylpentyl)-2-pyrrolidinecarboxylic acid A mixture of methyl (2S)-1-(1,2-dioxo-3,3-dimethylpentyl)-2-pyrrolidinecarboxylate (2.10 g; 8.23 mmol), in LiOH (15 mL), and methanol (50 mL) was stirred at 0° C. for 30 min and at room temperature overnight. The mixture was acidified to pH 1 with 1N HCl, diluted with water, and extracted into 100 mL of methylene chloride. The organic extract was washed with brine and concentrated to deliver 1.73 g (87%) of snow-white solid which did not require further purification. $^1$HNMR ($CDCl_3$): d 0.87 (r, 3H); 1.22, 1.25 (s, 3H each); 1.77 (dm, 2H); 2.02 (m, 2H); 2.17 (m, 1H); 2.25 (m, 1H); 3.53 (dd, 2H, J=: 10.4, 7.3); 4.55 (dd, 1H, J=8.6, 4.1).

Example 4

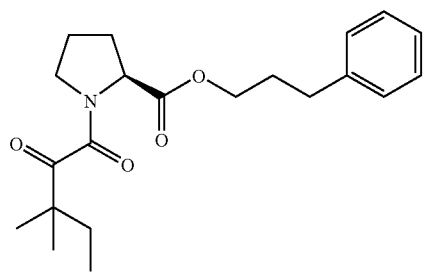

General procedure for the synthesis of prolyl esters. Exemplified for 3-phenyl-1-propyl (2S)-1-(3,3-dimethyl-1,2-dioxopentyl)-2-pyrrolidinecarboxylate.

A mixture of (2S)-1-(1,2-dioxo-3,3-dimethylpentyl)-2-pyrrolidine-carboxylic acid (600 mg; 2.49 mmol), 3-phenyl-1-propanol (508 mg; 3.73 mmol), dicyclohexylcarbodiimide (822 mg; 3.98 mmol), camphorsulphonic acid (190 mg; 0.8 mmol) and 4-dimethylaminopyridine (100 mg; 0.8 mmol) in methylene chloride (20 mL) was stirred overnight under a nitrogen atmosphere. The reaction mixture was filtered through Celite to remove solids and concentrated in vacuo, and the crude material was purified on a flash column (25% ethyl acetate in hexane) to obtain 720 mg (80%) of the product as a colorless oil. $^1$HNMR ($CDCl_3$): d 0.84 (t, 3H); 1.19 (s, 3H); 1.23 (s, 3H); 1.70 (dm, 2H); 1.98 (m, 5H); 2.22 (m 1H); 2.64 (m 2H); 3.47 (m 2H); 4.14 (m, 2H); 4.51 (d, 1H); 7.16 (m, 3H); 7.26 (m, 2H).

Example 5

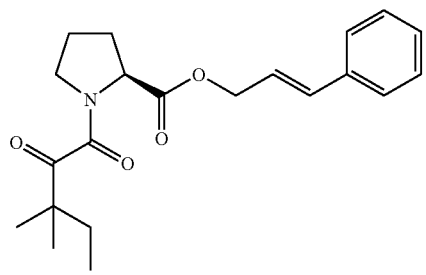

3-Phenyl-1-prop-2-(E)-enyl (2S)-1-(3,3-dimethyl-1,2-dioxopentyl)-2-pyrrolidinecarboxylate, 80%, ¹HNMR (360 MHz, CDCl₃): d 0.86 (t, 3H); 1.21 (s, 3H); 1.25 (s, 3H); 1.54-2.10 (m, 5H); 2.10-2.37 (m, 1H); 3.52-3.55 (m, 2H); 4.56 (dd, 1H, J=3.8, 8.9); 4.78-4.83 (m, 2H); 6.27 (m, 1H); 6.67 (dd, 1H, J=15.9); 7.13-7.50 (m, 5H). This compound was prepared by the method of Example 3 from (2S)-1-(1,2-dioxo-3,3-dimethylpentyl)-2-pyrrolidine-carboxylic acid.

Example 6

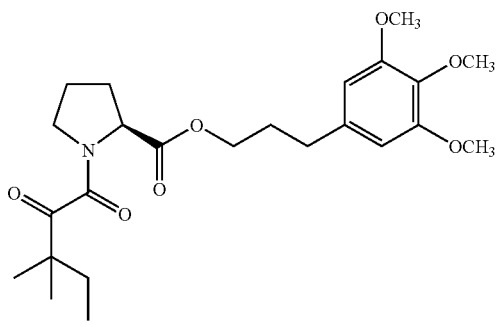

3-(3,4,5-Trimethoxyphenyl)-1-propyl (2S)-1-(3,3-dimethyl-1,2-dioxopentyl)-2-pyrrolidinecarboxylate, 61%, ¹HNMR (CDCl₃); d 0.84 (r, 3H); 1.15 (s, 3H); 1.24 (s, 3H); 1.71 (dm, 2H); 1.98 (m, 5H); 2.24 (m, 1H); 2.63 (m, 2H); 3.51 (t, 2H); 3.79 (s, 3H); 3.83 (s, 3H); 4.14 (m, 2H); 4.52 (m, 1H); 6.36 (s, 2H). This compound was prepared by the method of Example 3 from (2S)-1-(t,2-dioxo-3,3-dimethylpentyl)-2pyrrolidine-carboxylic acid.

Example 7

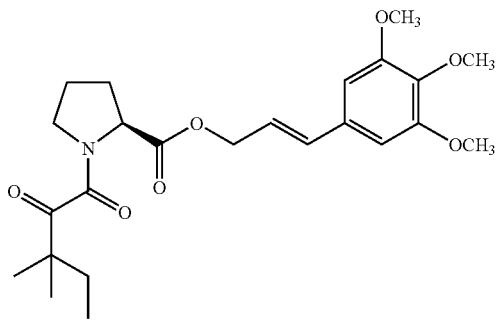

3-(3,4,5-Trimethoxyphenyl)-1-prop-2-(E)-enyl (2S)-1-(3,3-dimethyl-1,2-dioxopentyl)-2-pyrrolidinecarboxylate, 66%, ¹HNMR (CDCl₃): d 0.85 (r, 3H); 1.22 (s, 3H); 1.25 (s, 3H); 1.50-2.11 (m, 5H); 2.11-2.40 (m, 1H); 3.55 (m, 2H); 3.85 (s, 3H); 3.88 (s, 6H); 4.56 (dd, 1H); 4.81 (m, 2H); 6.22 (m, 1H); 6.58 (d, 1H, J=16); 6.63 (5, 2H). This compound was prepared by the method of Example 3 from (2S)-1-(1,2-dioxo-3,3-dimethylpentyl)-2-pyrrolidine-carboxylic acid.

Example 8

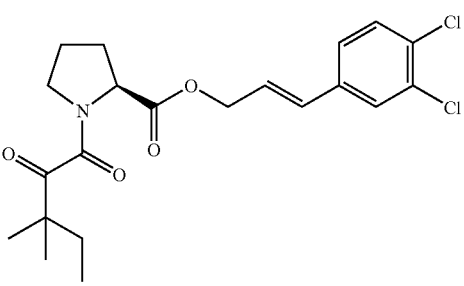

3-(4,5-Dichlorophenyl)-1-prop-2-(E)-enyl (2S)-1-(3,3-dimethyl-1,2-dioxopentyl)-2-pyrrolidinecarboxylate, 70%, ¹HNMR (CDCl₃): d 0.85 (t, 3H); 1.21 (s, 3H); 1.25 (s, 3H); 1.51-1.87 (m, 2H); 1.87-2.39 (m, 4H); 3.51-3.57 (m, 2H); 4.50-4.61 (dd, 1H, J=3.4, 8.6); 4.80 (d, 2H, J=6.0); 6.20-6.34 (m, 1H); 6.50-6.66 (d, 1H, J=16); 7.13-7.24 (dd, 1H, J=1.8, 8.3); 7.39 (d, 1H, J=8.3); 7.47 (s, 1H). This compound was prepared by the method of Example 3 from (2S)-1-(1,2-dioxo-3,3-dimethylpentyl)-2-pyrrolidine-carboxylic acid.

Example 9

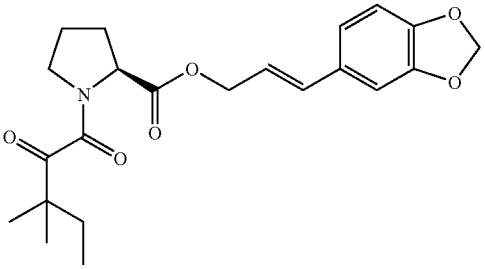

3-(4,5-Methylenedioxyphenyl)-1-prop-2-(E)-enyl (2S)-1-(3,3-dimethyl-1,2-dioxopentyl)-2-pyrrolidinecarboxylate, 82%, ¹HNMR (360 MHz, CDCl₃): d 0.86 (t, 3H); 1.22 (s, 3H); 1.25 (s, 3H); 1.60-2.10 (m, 5H); 3.36-3.79 (m, 2H); 4.53 (dd, 1H, J=3.8, 8.6); 4.61-4.89 (m, 2H); 5.96 (s, 2H); 6.10 (m, 1H); 6.57 (dd, 1H, J=6.2, 15.8); 6.75 (d, 1H, J=8.0); 6.83 (dd, 1H, J=1.3, 8.0); 6.93 (s, 1H). This compound was prepared by the method of Example 3 from (2S)-1-(1,2-dioxo-3,3-dimethylpentyl)-2-pyrrolidinecarboxylic acid.

Example 10

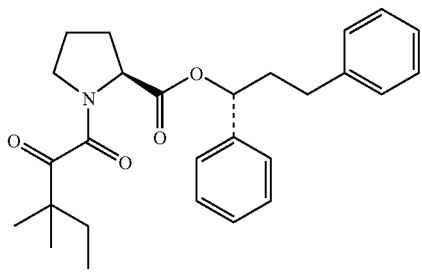

(1R)-1,3-Diphenyl-1-propyl (2S)-1-(3,3-dimethyl-1,2-dioxopentyl)-2-pyrrolidinecarboxylate, 90%, ¹HNMR (360 MHz, CDCl₃): d 3H); 1.20 (s, 3H); 1.23 (s, 3H); 1.49-2.39 (m, 7H); 2.46-2.86 (m, 2H); 3.25-3.80 (m, 2H); 4.42-4.82 (m, 1H); 5.82 (td, 1H, J=1.8, 6.7); 7.05-7.21 (m, 3H); 7.21-7.46 (m, 7H). This compound was prepared by the method of Example 3 from (2S)-1-(1,2-dioxo-3,3-dimethylpentyl)-2-pyrrolidinecarboxylic acid.

Example 11

The requisite substituted alcohols may be prepared by a number of methods known to those skilled in the art of organic synthesis. As described in Scheme II, substituted benzaldehydes may be homologated to phenyl propanols by reaction with methyl (triphenylphosphoranylidene) acetate to provide a variety of trans-cinnamates; these latter may be reduced to the saturated alcohols by reaction with excess lithium aluminum hydride, or sequentially by reduction of the double bond by catalytic hydrogenation and reduction of the saturated ester by appropriate reducing agents. Alternatively, the trans-cinnamates may be reduced to (E)-allylic alcohols by the use of diisobutylaluminum hydride.

Scheme II

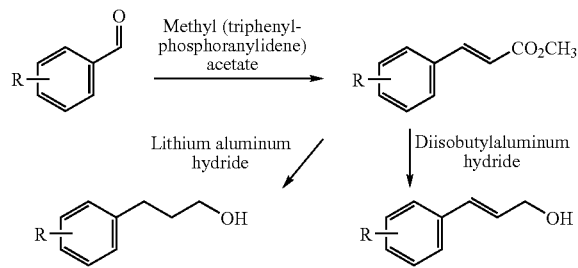

Longer chain alcohols may be prepared by homologation of benzylic and higher aldehydes. Alternatively, these aldehydes may be prepared by conversion of the corresponding phenylacetic and higher acids, and phenethyl and higher alcohols.

Example 12

General procedure for the synthesis of acrylic esters, exemplified for methyl (3,3,5-trimethoxy)-trans-cinnamate. A solution of 3,4,5-trimethoxybenzaldehyde (5.0 g; 25.48 mmol) and methyl (triphenyl-phosphoranylidene) acetate (10.0 g; 29.91 mmol) in tetrahydrofuran (250 mL) was refluxed overnight. After cooling, the reaction mixture was diluted with 200 mL of ethyl acetate and washed with 2 times 200 mL of water, dried, and concentrated in vacuo. The crude residue was chromatographed on a silica gel column, eluting with 25% ethyl acetate in hexane, to obtain 5.63 g (88%) of the cinnamate as a white crystalline solid, ¹HNMR (360 MHz, CDCl₃): d 3.78 (s, 3H); 3.85 (s, 6H); 6.32 (d, 1H, J=16); 6.72 (s, 2H); 7.59 (d, 1H, J=16).

Example 13

Methyl (4,5-dichloro)-trans-cinnamate, 80%, ¹HNMR (360 MHz, CDCl₃) d 3.79 (s, 3H); 6.40 (d, 1H, J=16.8); 7.32 (dd, 1H, J=1.5, 8.1); 7.44 (d, 1H, J=8.1); 7.56 (d, 1H, J=16); 7.58 (s, 1H). This compound was prepared by the method of Example 11 from 3,4,5-trimethoxybenzaldehyde.

Example 14

Methyl (4,5-methylenedioxy)-trans-cinnamate, 74%, ¹HNMR (360 MHz, CDCl₃): d 3.79 (s, 3H); 6.01 (s, 2H); 6.26 (d, 1H, J=16); 6.81 (d, 1H, J=7.9); 7.00 (d, 1H, J=8.2); 7.03 (s, 1H); 7.60 (d, 1H, J=16). This compound was prepared by the method of Example 11 from 3,4,5-trimethoxybenzaldehyde.

Example 15

Methyl (2-cyclohexyl)-(E)-acrylate, 80%, ¹HNMR (360 MHz, CDCl₃): d 1.12-1.43 (m, 5H); 1.52-1.87 (m, 5H); 2.12 (m, 1H); 3.71 (s, 3H); 5.77 (dd, 1H, J=1.2, 15.8); 6.92 (dd, 1H, J=6.8, 15.8). This compound was prepared by the method of Example 11 from 3,4,5-trimethoxybenzaldehyde.

Example 16

General procedure for the synthesis of saturated alcohols from acrylic esters. Exemplified for (3,4,5-trimethoxy)phenylpropanol.

A solution of methyl (3,3,5-trimethoxy)-trans-cinnamate (1.81 g; 7.17 mmol) in tetrahydrofuran (30 mL) was added in a dropwise manner to a solution of lithium aluminum hydride (14 mmol) in THF (35 mL), with stirring and under an Argon atmosphere. After the addition was complete, the mixture was heated to 75° C. for 4 hours. After cooling, it was quenched by the careful addition of 15 mL of 2N NaOH followed by 50 mL of water. The resulting mixture was filtered through Celite to remove solids, and the filter cake was washed with ethyl acetate. The combined organic fractions were washed with water, dried, concentrated in vacuo, and purified on a silica gel column, eluting with ethyl acetate to obtain 0.86 g (53%) of the alcohol as a clear oil, ¹HNMR (300 MHz, CDCl₃): d 1.23 (br, 1H); 1.87 (m, 2H); 2.61 (t, 2H, J=7.1); 3.66 (t, 2H); 3.80 (s, 3H); 3.83 (s, 6H); 6.40 (s, 2H).

Example 17

General procedure for the synthesis of trans-allylic alcohols from acrylic esters. Exemplified for (3,4,5-trimethoxy) phenylprop-2-(E)-enol.

A solution of methyl (3,3,5-trimethoxy)-trans-cinnamate (1.35 g; 5.35 mmol) in toluene (25 mL) was cooled to −10° C. and treated with a solution of diisobutylaluminum hydride in toluene (11.25 mL of a 1.0M solution; 11.25 mmol). The reaction mixture was stirred for 3 hrs at 0° C. and then quenched with 3 mL of methanol followed by 1N HCl until the pH was 1. The reaction mixture was extracted into ethyl acetate and the organic phase was washed with water, dried and concentrated. Purification on a silica gel column eluting with 25% ethyl acetate in hexane furnished 0.96 g (80%) of a thick oil, $^1$HNMR (360 MHz, CDCl$_3$): d 3.85 (s, 3H); 3.87 (s, 6H); 4.32 (d, 2H, J=5.6); 6.29 (dt, 1H, J=15.8, 5.7), 6.54 (d, 1H, J=15.8); 6.61 (s, 2H).

Example 18

(4,5-dichloro)phenylprop-2-(E)-enol, 89%, $^1$HNMR (360 Mhz; CDCl$_3$): d 1.55 (s, 1H); 4.34 (d, 2H, J=4.4); 6.36 (dt, 1H, J=15.9, 5.3); 6.54 (d, 1H, J=15.9); 7.20 (dd, 1H, J=8.3, 1.7); 7.38 (d, 1H, J=8.3); 7.45 (d, 1H, J=1.6). This compound was prepared by the method of Example 16 from (3,4,5-tri-methoxy)-trans-cinnamate.

Example 19

(4,5-methylenedioxy)phenylprop-2-(E)-enol, 80%, $^1$HNMR (360 MHz, CDCl$_3$): d 1.59 (br, 1H); 4.29 (br, 2H); 5.96 (s, 2H); 6.20 (dt, 1H, J=15.8, 5.9); 6.52 (d, 1H, J=15.8); 6.76 (d, 1H, J=8.0); 6.82 (dd, 1H, 38 J=8.0, 1.2); 6.93 (d, 1H, J=1.2). This compound was prepared by the method of Example 16 from (3,4,5-tri-methoxy)-trans-cinnamate.

Example 20

Phenylprop-2-(E)-enol, 85%, $^1$HNMR (360 MHz, CDCl$_3$): d 1.72 (br, 1H); 4.31 (d, 2H, J=5.7); 6.36 (dt, 1H, J=15.9, 5.7); 6.61 (d, 1H, J=15.9); 7.0.2-7.55 (m, 5H). This compound was prepared by the method of Example 16 from (3,4,5-tri-methoxy)-trans-cinnamate.

Example 21

Alcohols containing a substituent at the 1-position of the side chain may be conveniently prepared by addition of appropriate nucleophiles to aldehydes, as described in Scheme III. In cases where optically active substituted alcohols are desired, the racemic alcohols may be oxidized to prochiral ketones and subjected to asymmetric reduction by one of several methods well known to those skilled in the art.

Scheme III

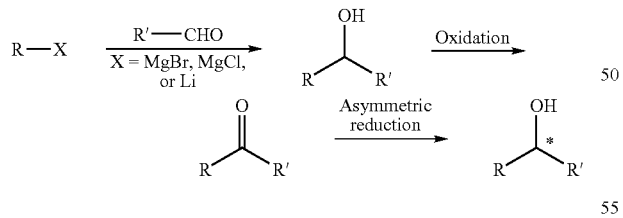

Example 22

General procedure for the preparation of 1-substituted alkanols, exemplified for the synthesis of 1,3-diphenylpropanol.

A solution of 2-(bromoethyl)benzene (17.45 g; 94.3 mmol) in 50 mL of dry diethyl ether was added dropwise, under a nitrogen atmosphere, to a stirred slurry of magnesium turnings (2.50 g; 102.8 mmol) in 50 mL of ether. The mixture was initially heated with a heat gun until reflux had become self-sustaining. After the addition was complete, the mixture was heated externally for 30 min to maintain reflux. A solution of 10.01 g (94.3 mmol) of benzaldehyde in 20 mL of ether was then added dropwise, and reflux was continued for 30 min. After cooling, the reaction mixture was poured into 150 mL of saturated ammonium chloride and extracted into ethyl acetate. The crude material obtained upon removal of the solvent was purified on a flash column, eluting with 5% ethyl acetate/hexane to 20% ethyl acetate, to obtain 13.73 g (69%) of the alkanol as a light yellow oil, $^1$HNMR (360 MHz, CDCl$_3$): d 1.93-2.30 (m, 3H); 2.70-2.90 (m, 2H); 4.72 (br, 1H); 7.19-7.27 (m, 3H); 7.27-7.36 (m, 3H); 7.36-7.47 (m, 4H).

Example 23

General procedure for conversion of racemic 1-substituted alkanols to optically active 1-substituted alkanols via prochiral ketones. Exemplified for (1R)-1,3-diphenyl-1-propanol.

A solution of racemic 1,3-diphenyl-1-propanol (1.26 g; 5.94 mmol) was dissolved in 10 mL of acetone, and Jones reagent was added until persistence of the orange color. After stirring for 30 min, the reaction was quenched by adding 2 mL of 2-propanol. The solvent was decanted away from the precipitated solids, which were washed with ethyl acetate. The combined organic fractions were washed with 2 times 20 mL of water, dried and concentrated. The crude product was filtered through a plug of silica gel, eluting with 25% ethyl acetate/hexane, to obtain 1.07 g (86%) of 1,3-diphenylpropanone as a white crystalline solid, $^1$HNMR (360 MHz, CDCl$_3$): d 3.09 (t, 2H, J=8.1); 3.33 (t, 2H, J=8.1); 7.29 (m, 5H); 7.49 (m, 3H); 7.98 (m, 2H).

A solution of 1,3-diphenylpropanone (1.07 g; 5.09 mmol) in tetrahydrofuran (10 mL) was cooled to −23° C. and treated with an asymmetric reducing agent, (+)-B-chlorodiisopinocampheyl-borane (1.80 g; 5.60 mmol) in 20 mL THF, and the resulting solution was allowed to stand overnight at −23° C. After evaporating to dryness, the residue was treated with ether (65 mL) and diethanolamine (1.0 g) and stirred for 3 hrs. The mixture was then filtered to remove solids and concentrated, and the residue was purified using gradient elution (5% ethyl acetate/hexane to 10% ethyl acetate) on a silica gel column to obtain 660 mg (61%) of (1R)1,3-diphenyl-1-propanol as a crystalline white solid, $^1$HNMR (360 MHz, CDCl$_3$): d 1.95-2.15 (m, 3H); 2.59-2.78 (m, 2H); 4.65 (dd, 1H, J=5.4, 7.8); 7.14-7.35 (m, 10H).

Example 24

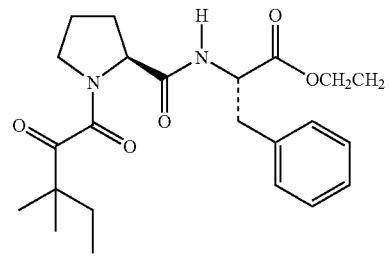

General procedure for the synthesis of prolyl dipeptides, exemplified for 1-[1-(3,3-dimethyl-1,2-dioxopentyl-L-proline]-L-phenylalanine ethyl ester A mixture of (2S)-1-(1,2-dioxo-3,3-dimethylpentyl)-2-pyrrolidinecarboxylic acid (1.17 g; 4.85 mmol), L-phenylalanine ethyl ester hydrochloride (1.23 g; 5.33 mmol), dicyclohexylcarbo-diimide (1.10 g, 5.33 mmol) and 4-dimethylaminopyridine (60 mg (4.85 mmol) in methylene chloride (25 mL) was treated with triethylamine (1 mL; 726 mg; 7.17 mmol) and stirred overnight. The mixture was filtered through Celite to remove solids and concentrated, and the crude material from removal of the solvent was purified on a silica gel column eluting with 30% ethyl acetate/hexane to obtain 2.02 g of 1-[1-(3,3-dimethyl-1,2-dioxopentyl)-L-proline]-L-phenylalanine ethyl ester, 100%, $^1$HNMR (360 MHz, CDCl$_3$): d 0.87 (t, 3H); 1.16-1.28 (m, 9H); 1.58-1.91 (m, 5H); 2.33 (m, 1H); 3.07-3.20 (m, 2H); 3.38-3.41 (m, 2H); 4.11-4.18 (m, 4H); 4.55 (d, 1H, J-6.5); 4.78-4.80 (m, 1H); 7.15 (br d, 1H); 7.19 (m, 5H).

The invention being thus described, it will be obvious that the same may be varied in many ways. Such variations are not to be regarded as a departure from the spirit and scope of the invention and all such modification are intended to be included within the scope of the following claims.

What is claimed is:

1. A method of making (2S)-1-(1,2-dioxo-3,3-dimethylpentyl)-2-pyrrolidinecarboxylic acid, comprising the steps of:
   i) reacting L-proline methyl ester hydrochloride with methyl oxalyl chloride to form methyl (2S)-1-(1,2-dioxo-2-methoxyethyl)-2-pyrrolidinecarboxylate;
   ii) reacting the methyl (2S)-1-(1,2-dioxo-2-methoxyethyl)-2-pyrrolidinecarboxylate obtained in step (i) with 1,1-dimethylpropylmagnesium chloride to form methyl (2S)-1-(1,2-dioxo-3,3-dimethylpentyl)-2-pyrrolidinecarboxylate;
   iii) reacting the methyl(2S)-1-(1,2-dioxo-2-methoxyethyl)-2-pyrrolidinecarboxylate obtained in step (ii) with LiOH to form (2S)-1-(1,2-dioxo-3,3-dimethylpentyl)-2-pyrrolidinecarboxylic acid.

2. The method as recited in claim 1, wherein step (i) is performed under an inert atmosphere.

3. The method as recited in claim 2, wherein the inert atmosphere is a nitrogen atmosphere.

4. The method as recited in claim 2, wherein step (i) is done in a polar aprotic solvent.

5. The method as recited in claim 4, wherein the polar aprotic solvent is methylene chloride.

6. The method as recited in claim 4, wherein step (ii) is done in a polar aprotic solvent.

7. The method as recited in claim 6, wherein the polar aprotic solvent is tetrahydrofuran.

8. The method as recited in claim 6, wherein step (iii) is done in a polar protic solvent.

9. The method as recited in claim 8, wherein the polar protic solvent is methanol.

10. A method of making a pyrrolidinyl alkyl oxamate, comprising the steps of:
    i) reacting L-proline methyl ester hydrochloride with methyl oxalyl chloride to form methyl (2S)-1-(1,2-dioxo-2-methoxyethyl)-2-pyrrolidinecarboxylate;
    ii) reacting methyl (2S)-1-(1,2-dioxo-2-methoxyethyl)-2-pyrrolidinecarboxylate with a carbon nucleophile of the form R—Li or R—MgX, wherein:
    X is a halogen; and
    R is selected from the group consisting of a $C_1$-$C_9$ straight or branched chain alkyl or alkenyl group optionally substituted with $C_3$-$C_8$ cycloalkyl, $C_3$ or $C_5$ cycloalkyl, $C_5$-$C_7$ cycloalkenyl, $Ar_1$, where said alkyl, alkenyl, cycloalkyl or cycloalkenyl groups may be optionally substituted with $C_1$-$C_4$ alkyl, $C_1$-$C_4$ alkenyl, or hydroxy, where $Ar_1$ is selected from the group consisting of 1-naphthyl, 2-naphthyl, 2-indolyl, 3-indolyl, 2-furyl, 3-furyl, 2-thiazolyl, 2-thienyl, 3-thienyl, 2-, 3-, 4-pyridyl, and phenyl, having one to three substituents which are independently selected from the group consisting of hydrogen, halo, hydroxyl, nitro, trifluoromethyl, $C_1$-$C_6$ straight or branched alkyl or alkenyl, $C_1$-$C_4$ alkoxy or $C_1$-$C_4$ alkenyloxy, phenoxy, benzyloxy, and amino.

11. The method as recited in claim 10 wherein step (ii) is done in a polar aprotic solvent.

12. The method as recited in claim 11, wherein the polar aprotic solvent is tetrahydrofuran.

13. The method as recited in claim 10, wherein step (i) is performed under an inert atmosphere.

14. The method as recited in claim 13, wherein the inert atmosphere is a nitrogen atmosphere.

15. The method as recited in claim 13, wherein step (i) is done in a polar aprotic solvent.

16. The method as recited in claim 15, wherein the polar aprotic solvent is methylene chloride.

17. The method as recited in claim 10 wherein R is a $C_1$-$C_9$ straight or branched chain alkyl.

\* \* \* \* \*